(12) United States Patent
Collins et al.

(10) Patent No.: US 6,814,707 B2
(45) Date of Patent: Nov. 9, 2004

(54) BLOOD COLLECTION SAFETY DEVICE

(76) Inventors: Margie M. Collins, 4104 Garth Rd. SE., Huntsville, AL (US) 35802; Cary C. Collins, 4104 Garth Rd. SE., Huntsville, AL (US) 35802

( * ) Notice: Subject to any disclaimer, the term of this patent is extended or adjusted under 35 U.S.C. 154(b) by 120 days.

(21) Appl. No.: 10/175,219

(22) Filed: Jun. 19, 2002

(65) Prior Publication Data

US 2003/0004437 A1 Jan. 2, 2003

Related U.S. Application Data

(60) Provisional application No. 60/299,498, filed on Jun. 20, 2001.

(51) Int. Cl.[7] .............................. A61B 5/00; B65D 81/00
(52) U.S. Cl. ..................................................... 600/576
(58) Field of Search ................................ 600/576, 579, 600/577; 604/110, 195, 198, 205, 240

(56) References Cited

U.S. PATENT DOCUMENTS

| | | | | |
|---|---|---|---|---|
| 4,915,702 A | * | 4/1990 | Haber | 604/198 |
| 5,374,250 A | * | 12/1994 | Dixon | 604/110 |
| 5,423,758 A | * | 6/1995 | Shaw | 604/110 |
| 5,437,639 A | * | 8/1995 | Malenchek | 604/110 |
| 5,938,622 A | * | 8/1999 | Chen | 600/576 |
| 6,579,245 B1 | * | 6/2003 | Pakszys | 600/579 |

* cited by examiner

Primary Examiner—Max Hindenburg
Assistant Examiner—Brian Scott Szmal
(74) Attorney, Agent, or Firm—Curtis W Dodd

(57) ABSTRACT

A blood collection device includes a syringe assembly containing a slidable needle assembly within the cavity of a syringe body. The syringe body has a syringe top for receiving a seal assembly wherein the seal assembly is reversibly locked to the top of the syringe top. Within the insertable tube of the seal assembly is an occluding seal secured within the insertable cylinder with retaining rings. The occluding seal allows blood to flow from on end of a double pointed needle into a fully inserted collection tube. When the collection tube is removed the occluding seal keeps blood from flowing into the cavity of the insertable cylinder.

14 Claims, 6 Drawing Sheets

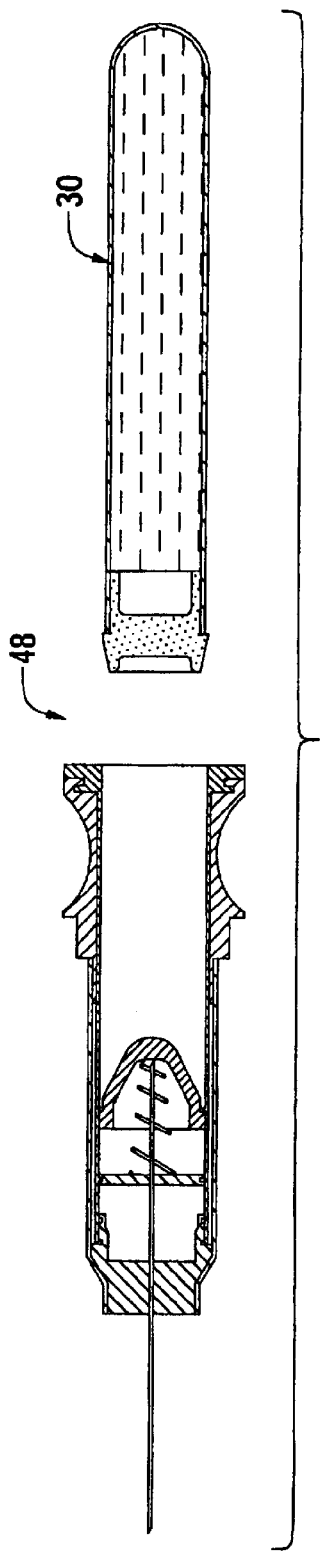
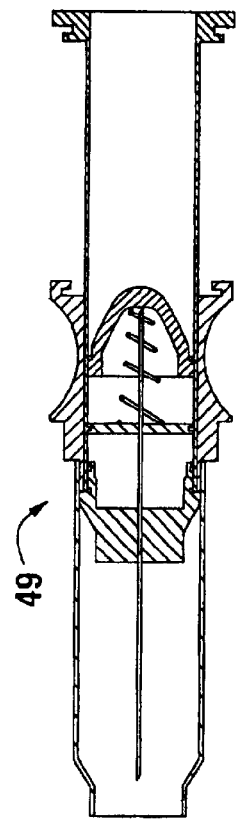
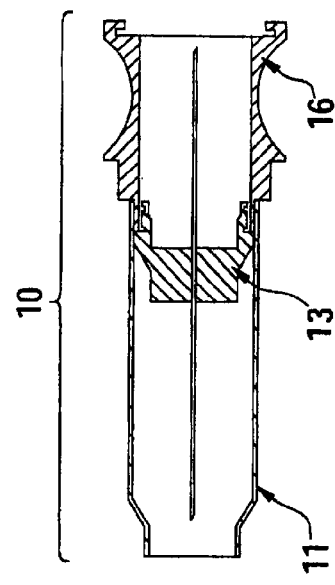
FIG. 6
FIG. 7
FIG. 8

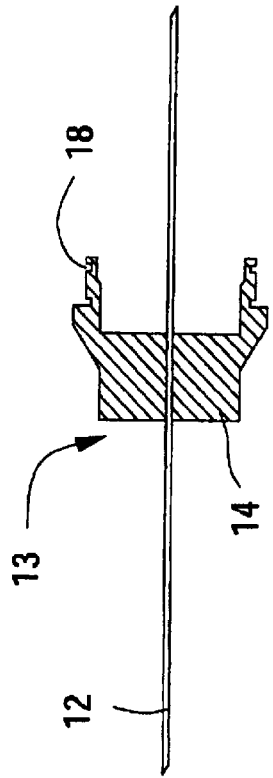
FIG. 10
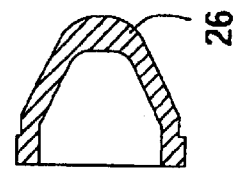
FIG. 14
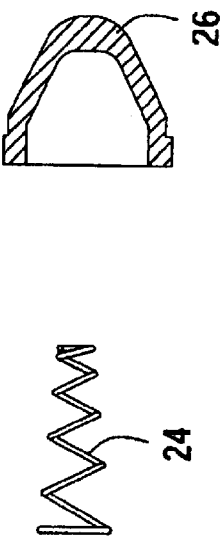
FIG. 13
FIG. 12
FIG. 9
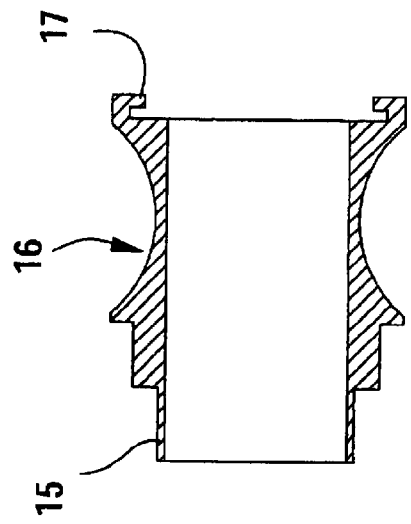
FIG. 11

BLOOD COLLECTION SAFETY DEVICE

PRIORITY APPLICATION

This application is related to U.S. Provisional Application Serial No. 60/299,498 filed on Jun. 20, 2001, entitled "BLOOD COLLECTION SAFETY DEVICE" and assigned to all the above named inventors, and incorporated by reference herein, with priority claimed for all commonly disclosed subject matter.

BACKGROUND OF THE INVENTION

1. Field of the Invention

The present invention relates to a device for collecting blood having a needle containment safety apparatus and method for protecting medical personnel and others from the risk of accidental percutaneous needlestick injuries.

2. Background of the Invention

Because there are risks associated with accidental needle sticks to a medical person collecting blood, a variety of safety blood collection syringes have been developed. Most of these syringes have a safety shield that slides over an extended needle after the blood is collected. The safety shield may be held in place by a spring, friction, locking tabs or other means. However many of these safety devices require the person to manually place or move the protective shield over the needle thereby providing an opportunity, though slight, for an accidental needle stick.

A safety blood collection and transfer device of McCallister, U.S. Pat. No. 6,360,011 is designed to accept a vacuum type blood tube (vacutainer) for collecting blood. McCallister's invention requires two double pointed needles coupled to each end of a plunger with a hollow core. In addition, a cylindrical syringe and a blood tube holder are required. However the user is required to remove and replace a needle cover providing a slight chance of a stick.

The hypodermic safety device of Lockwood, U.S. Pat. No. 5,403,286 is an example of a device having an extendable cover for user protection. Lockwood's invention has an extension apparatus attached to a standard hypodermic needle that places or disposes a protective cover over an extended needle when a compressed spring is manually released. Lockwood's patent, in a prior art review, discusses much of the prior art related to protective covers and then describes the improvements provided by his invention.

There is a need to new approach for a blood collection device. The present invention does not use an extendable cover, but retracts the needle within a disposable syringe body. A novel device for blood collection, described herein, is less complex than existing and convention devices, is easy to use, and should cost less than most existing devices.

SUMMARY OF THE INVENTION

A blood collection device, that is adapted for use with conventional blood collection tubes ("vacutainer") and does not have the complexity of prior art blood collection syringes, has been invented. The blood collection device is easy to operate and is an improvement over prior art devices.

A blood collection device for use with a conventional collection tube is comprised of a syringe assembly and a sealing assembly. The syringe assembly comprises a syringe body having a tapered distal end and adapted for holding a slidable needle assembly wherein the needle assembly comprises a needle carrier and a double pointed needle, the syringe assembly further has a syringe top, securely attached to the proximal end of the syringe body, for containing the needle assembly within the syringe body. The sealing assembly has an occluding seal inside a cavity of an insertable cylinder that is adapted for pushing the needle assembly towards the distal end of the syringe body or for pulling the needle assembly towards the proximal end of the syringe body. When the occluding seal and seal of the collection tube are punctured by the proximal point of the needle (the distal point of the needle is used to puncture a vein), as the collection tube is pushed into place for blood collection, blood flows into the collection tube. When the collection tube is removed from the insertable cylinder the occluding seal blocks (occludes) blood from contaminating the proximal end of the blood collection device.

BRIEF DESCRIPTION OF THE DRAWINGS

The invention can be better understood with reference to the following drawings. The elements of the drawings are not necessarily to scale relative to each other, emphasis instead being placed upon clearly illustrating the principles of the invention. Furthermore, like reference numerals designate corresponding parts throughout several views.

FIG. 6 illustrates the removal stage of the blood collection device, stage four;

FIG. 7 illustrates the safety stage of the blood collection device, stage five;

FIG. 8 illustrates details of the syringe assembly of FIG. 1;

FIG. 9 illustrates details of the syringe body of FIG. 1;

FIG. 10 illustrates details of the needle assembly of FIG. 1;

FIG. 11 illustrates details of the syringe top of FIG. 1;

FIG. 12 illustrates details of the flat seal of FIG. 1;

FIG. 13 illustrates details of the spring of FIG. 1;

FIG. 14 illustrates details of the conical seal of FIG. 1;

DETAILED DESCRIPTION OF THE INVENTION

Although those skilled in the art may apply variations to the present invention as characterized in the detailed description, such variations would fall within the scope of the present invention.

The blood collection safety device as described in the figures is fabricated of materials typically used for medical devices of the same type, such as syringes for injecting medication, traditional blood collecting devices and the like. All elements of the device and the assembled device would meet the requirements of corresponding government and medical agencies provided for protection of those practicing and receiving medical services. As new materials are developed that meet the needs for each and every part of the safety device, the device fabricated with the new materials would fall within the scope of the present invention (and claims when a utility application is completed).

Figure 1:
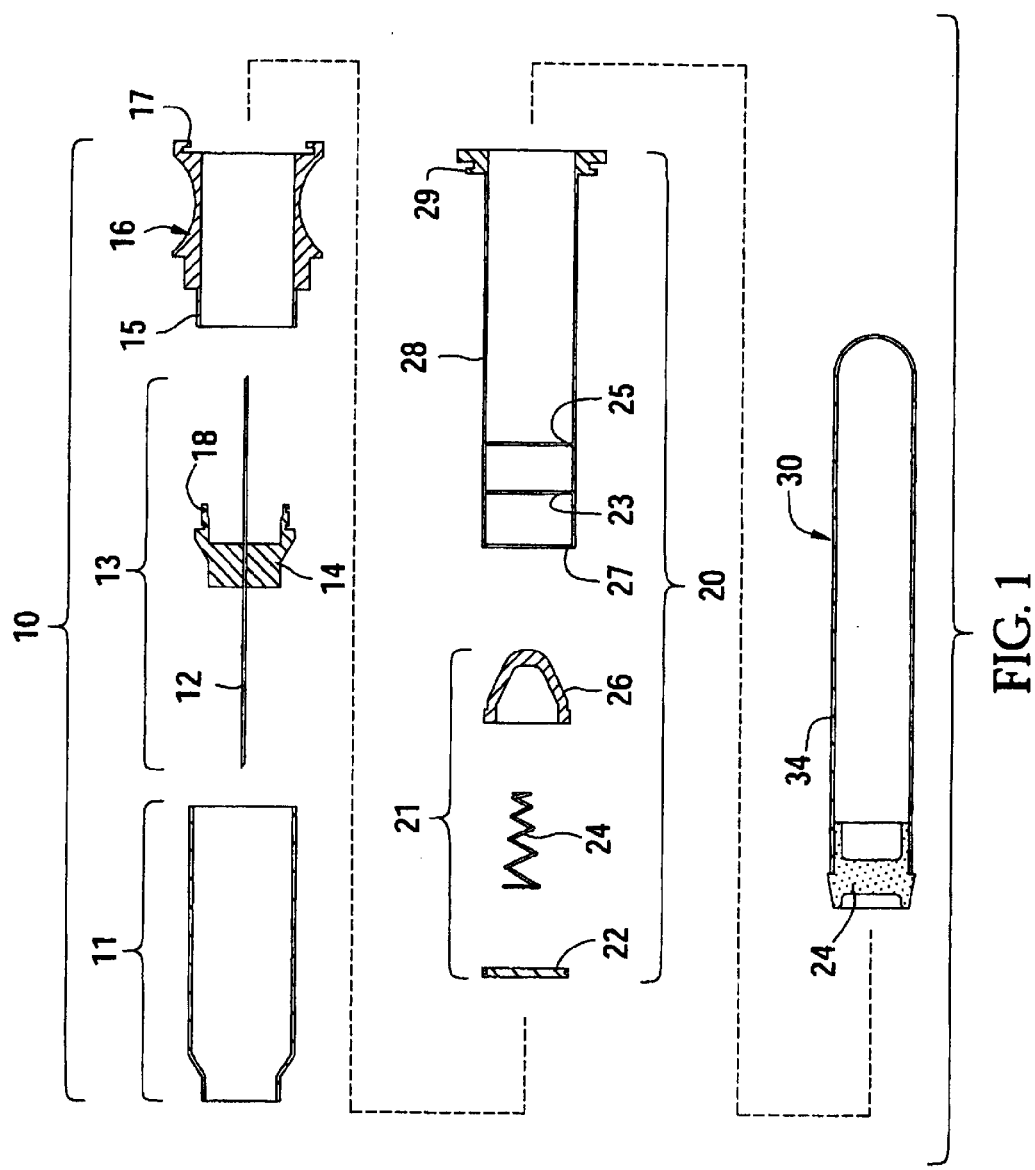
FIG. 1 illustrates an assembly arrangement for the essential elements of the blood collection device in accordance with the present invention.
Figure 2:
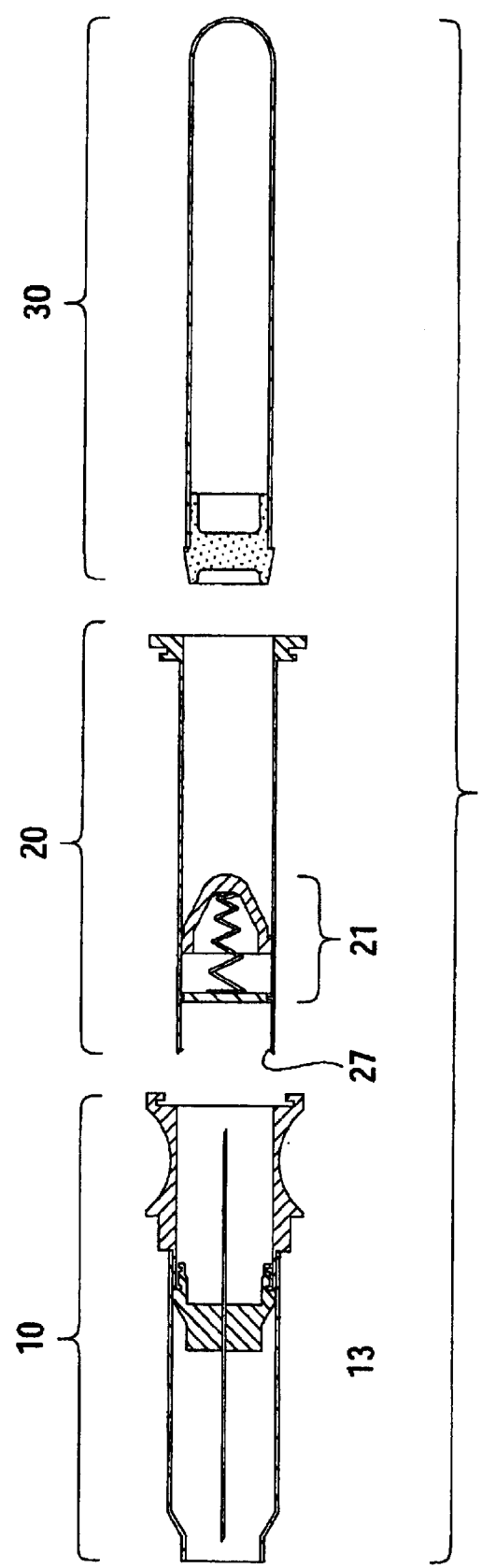
FIG. 2 shows a partially assembled collection device having the elements shown in FIG. 1.

Referring now to FIG. 1 there is shown a drawing illustrating essential elements of the present invention. A syringe body 11 is cylinder with a tapered end, the distal end, and a proximal end, no tapering. The proximal end is adapted to receive a needle assembly 13 comprising a needle carrier 14 and a needle 12. After the needle assembly is inserted in and contained within the syringe body 11 a syringe top 16 is bonded via an insertable edge 15 to the inside of the proximal end of the syringe body 11. Note that the syringe top 16 has a lock channel 17 on the proximal end of the syringe top for receiving a tab which will be described below. A syringe assembly 10 as shown in FIG. 2 is provided when all elements 11, 13 and 16 are assembled.

Figure 3:
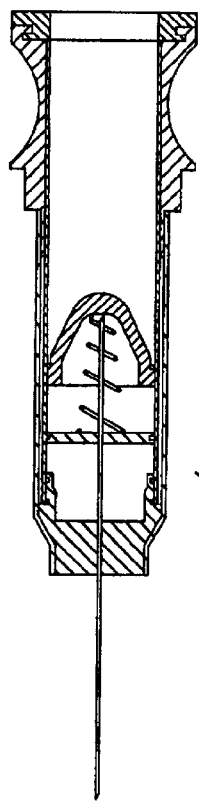
FIG. 3 illustrates the assembled stage of the blood collection device, stage one.

Still referring to FIG. 1 there is a seal assembly 20 comprised of an insertable cylinder 28 with a twist tab 29, where the insertable assembly encloses or contains an occluding seal 21. The occluding seal is comprised of a flat seal 22, a spring 24 and a conical seal 26 in an arrangement as shown in FIG. 1. The occluding seal fits inside the seal assembly 20 as shown in FIG. 2. The twist tab 29 of the seal assembly 20 engages the lock channel 17 of the syringe assembly 10 in a twisting motion and may be referred to as a bayonet connection. FIG. 3 illustrates the assembled invention comprising the seal assembly 20 inserted in the syringe assembly 10. Other locking methods may also be used and fall within the scope of the present invention.

FIG. 3 represents a first stage, an assembled stage 42, of five stages (FIGS. 3–7) that illustrate the operation of the blood collection safety device in accordance with the present invention. The assembled stage, stage 1, is accomplished just before blood is to be collected. To reach the assembled stage 42 the needle 12, which has been advanced by pushing the seal assembly 20 in the distal direction such that the needle is extending outward from the distal end of the syringe assembly 10, is inserted in a blood vessel using the appropriate medical procedure. When blood is observed flowing from the proximal lumen of the needle 12 into the cavity between the punctured flat seal 22 and conical seal 26, the seal assembly 20 is further advanced until the proximal lumen is embedded in the distal surface of the conical seal 26 thereby stopping blood flow, concomitantly the lock tab 27 snaps into lock groove 18 providing an irreversible connection. After the twist tab 29 is rotated, for a reversible lock, into the lock channel 17 (a bayonet type coupling) the assembled stage is complete.

Figure 4:
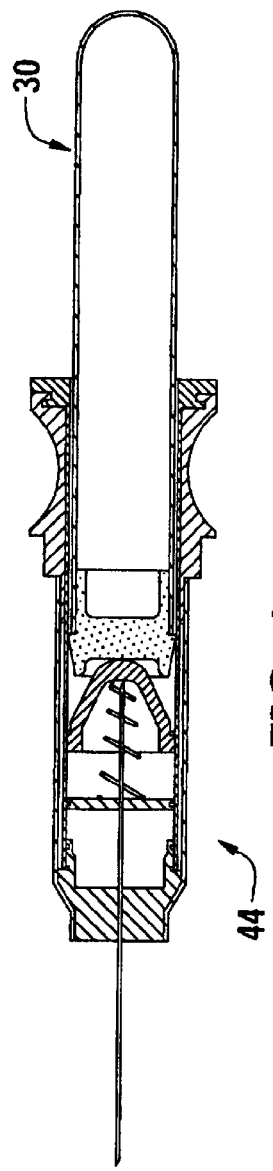
FIG. 4 illustrates the pre-collection stage of the blood collection device, stage two.
Figure 5:
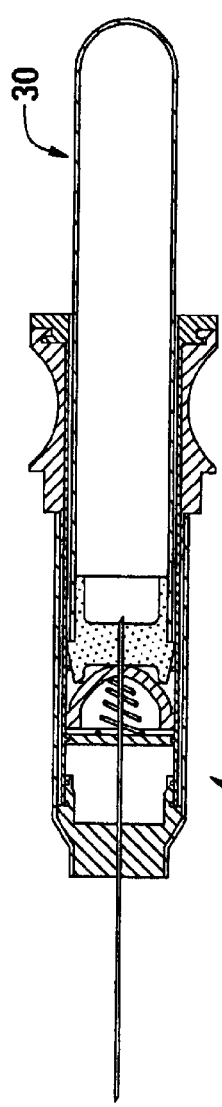
FIG. 5 illustrates the collecting stage of the blood collection device, stage three.
Figure 15:
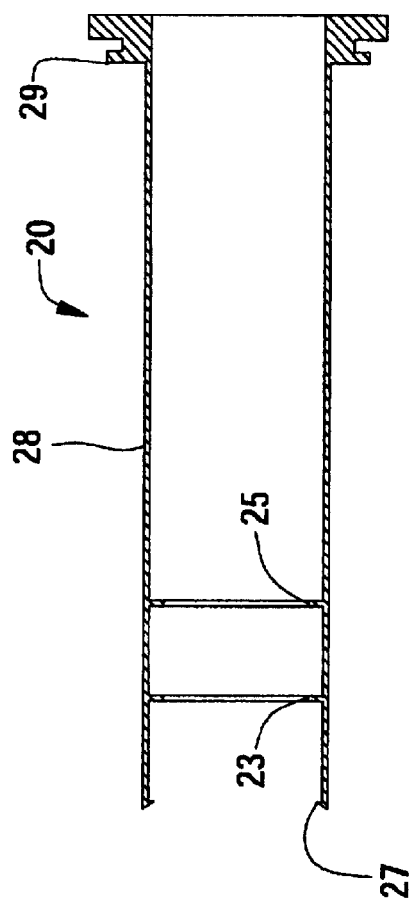
FIG. 15 illustrates details of the insertable cylinder of FIG. 1.
Figure 16:
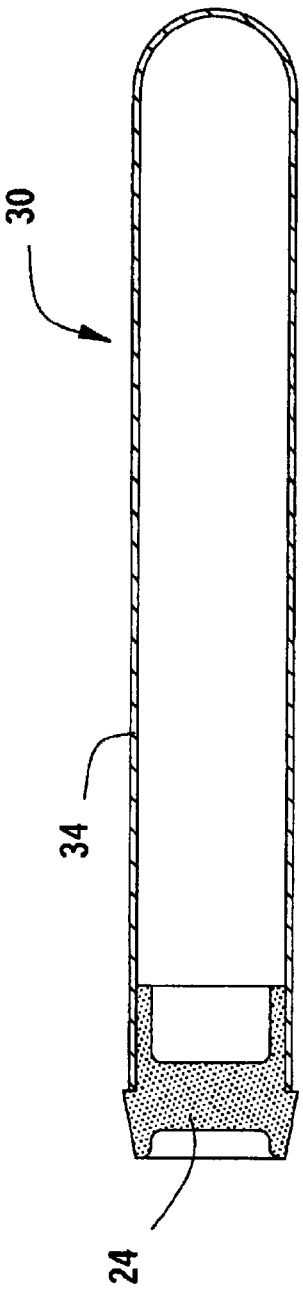
FIG. 16 illustrates details of the blood container of FIG. 1.

Next, for stage 2 or a pre-collection stage 44, the vacutainer 30 (collection tube) is positioned within the seal assembly 20 as shown in FIG. 4. Note that the distal end of the vacutainer seal 32 rests against the proximal end of the conical seal 26 and there is no blood flow.

Next for stage 3, a collecting stage 46, the vacutainer is pushed or urged towards the occluding seal 21. When sufficient force is applied to the vacutainer, the proximal point of the needle 12 punctures both the conical seal 26 and the vacutainer seal 32. The proximal point of the needle 12, as shown, goes through the center of the spring 24 and the spring is compressed as long as a force is applied to the vacutainer. When the vacutainer 30 is filled with blood and the force is removed, the spring 24 goes from a compressed position to an extended or normal position and the vacutainer is withdrawn or removed from the seal assembly 20 as shown in FIG. 6 stage 4, a removal stage 48. The spring goes from a compressed mode to an uncompressed mode (the original mode) causing the conical seal 26 to stop blood flow from entering the open section of the seal assembly. Other sealing methods may also be used and fall within the scope of the present invention. The process comprising stages 2–4 is repeated if more than one vacutainer of blood is needed. When all the required blood has been collected the needle is removed from the blood vessel as described in FIG. 7.

FIG. 7 illustrated a stage 5, a safety stage 49, for the collection device. In order to reach the safety stage the bayonet connection is released and the seal assembly is pulled in a proximal direction as shown in FIG. 7. The lock tab 27, being irreversibly engaged in the lock groove 18 pulls the needle from the vein supplying blood and pulls the needle assembly 14 inside the syringe body, where the needle assembly (and hence the needle) is locked and held in a safe position within the syringe assembly and seal assembly. When the needle assembly is contained within the syringe assembly, medical and other persons are protected from the possibility of a needle stick. When in the safety stage 49, the needle now contaminated cannot stick or cause injury to medical or other persons.

The remaining figures, FIGS. 8–16, provide more details of the elements shown in FIG. 1 and further assist a person skilled in the art with the necessary details to build the blood collection safety device of the present invention. The inventor has provided an embodiment that would allow a person skilled in the art to build, fabricate or make the blood collection safety device. However the inventor believes those making some variation in the invention, such as for example, having different locking arrangements, changing shapes of seals, using different materials and making other non-substantial changes would be practicing the invention.

OPERATIONAL INSTRUCTIONS FOR THE BLOOD COLLECTION DEVICE

Operational instructions for the blood collection device are provided to illustrate how each of the elements work together to collect blood in a blood container such as a vacutainer. The operation is described in distinct steps or stages that are illustrated in FIGS. 3–7. It may also be helpful to refer to FIGS. 1 and 2 for viewing the details of each of the elements.

For the description of the operation of the blood collection device consider first the elements:
syringe assembly 10;
needle assembly 13;
seal assembly 20;
blood container 30 (vacutainer); and
occluding seal 21 with compressible mechanism First the distal end of seal assembly 20 is inserted into the proximal opening of syringe assembly 10, step 1. The user then pushes or urges the seal assembly 20 in the distal direction.

As the seal assembly 20 goes forward the lock tab 27 of seal assembly pushes the needle assembly 13 down the barrel (the cavity) of the syringe body 11 until the distal end of the needle 12 is fully extruded from the opening at the distal tapered end of the syringe body. During this operation, step 2, the proximal end of the needle 12 penetrates the flat seal 22 placing the proximal end of the needle in the space between the flat seal 22 and the conical seal 26.

Next, step 3, the distal end of the needle 12 is inserted into a vein and when a positive blood flow is detected at the proximal lumen of needle 12 the seal assembly 20 is moved farther distally until there is an irreversible engagement with the lock groove 18 of the needle carrier 14 and the lock tab 27 of the seal assembly 20. At this stage the proximal lumen of needle 12 partially penetrates the conical seal 26 and causing (by blocking) blood flow to cease. The distal locking twist tab 29 is reversibly engaged (bayonet type locking mechanism) with proximal lock channel 17 of the syringe top 16.

For step 4, the distal end of a standard vacutainer 34 (collection tube) is then inserted into the proximal opening of seal assembly 20 and moved in a distal direction until the distal seal of the vacutainer contacts the proximal aspect of the conical seal 26 of the occluding seal 21. Additional distal pressure on the vacutainer 34 compresses the conical seal 26 exposing the proximal end of the needle 12 and causing the proximal end of needle 12 to penetrate the distal end of vacutainer seal 32 of the vacutainer. Blood flow now resumes (it was earlier blocked) at this point and blood collects within the cavity of the vacutainer 34.

When sufficient (the desired amount) blood has been collected in the vacutainer 34, the filled vacutainer is removed, step 5, from the combined seal assembly 20 and syringe assembly 10. Concomitantly, the conical seal 26 decompresses (spring 24 expands) and moves proximally to again occlude blood flow from the lumen of the proximal end of the needle 12.

If more blood is needed, step 6 (optional), additional vacutainers are used by repeating steps 4 through 5.

When the blood collection procedure has been completed, and while the needle remains in the vein, the seal assembly 20 is disengaged (it was earlier reversibly engaged) from the syringe assembly 10 by rotating the bayonet type locking mechanism and withdrawing the seal assembly 20 in a proximal direction, step 7. The needle assembly 13, being irreversibly locked with the locking tabs 27 of the seal assembly 20, is concomitantly and safely withdrawn into the cavity of syringe body 11. This action removes the needle from the target tissue without the contaminated needle being exposed to the health care provider. The distal insertable edge 15 of the syringe top 16, prevents the needle carrier 14 from being withdrawn from the syringe assembly 10 thereby further enhancing the safety of this blood collection device.

All such modifications and variations of the embodiments of the blood collection device are intended to be included herein and are within the scope of this disclosure that is protected by the following claims.

We claim:

1. A blood collection safety syringe for use with a collection tube having a seal, the syringe comprising:
   a syringe assembly comprising a syringe body with a hollow barrel and a tapered distal end, the syringe body adapted for enclosing a needle assembly wherein the needle assembly comprises a needle carrier and a double pointed needle extending outward from each end of the carrier, the syringe assembly further having a syringe top secured to the proximal end of the syringe body; and
   an insertable seal assembly comprising an insertable cylinder and an occluding seal secured within the distal end of the insertable cylinder, further the insertable cylinder has a reversible locking means on its proximal end for locking the cylinder to the syringe top, the insertable cylinder further having an irreversible locking means for securing the seal assembly to the needle assembly causing the needle assembly to move with the seal assembly when the insertable cylinder is unlocked from the syringe top and pulled in the proximal direction.

2. The blood collection device of claim 1 wherein the reversible locking means is a bayonet type locking mechanism.

3. The blood collection device of claim 1 wherein the occluding seal comprises a flat seal and a conical seal adapted to contain a compressible spring.

4. The blood collection device of claim 1 wherein the irreversible locking means comprises a lock tab at the distal end of the insertable cylinder and a lock groove on the outer edge of the proximal end of the needle carrier.

5. The blood collection device of claim 4 wherein one or more retaining rings secures the occluding seal within the insertable cylinder.

6. A blood collection device for collecting blood in a collection tube, the blood collection device comprising:
   a syringe assembly having a syringe body with a cavity, the syringe body having a taper at its distal end, the syringe assembly further having a slidable needle assembly axially holding a double pointed needle contained in the cavity by a syringe top on the proximal end of the syringe body and the taper; and
   a seal assembly adapted for insertion into the syringe body, the seal assembly having a means for allowing blood to flow in the distal lumen of the needle from a venipuncture and through the lumen end of the needle into the fully inserted collection tube, the seal assembly further having a means for pulling the needle assembly within the syringe body when blood collection is completed, thereby removing the chance of a needle stick.

7. The blood collection device of claim 6 wherein the needle assembly has a lock groove that snaps to a lock tab on the seal assembly.

8. The blood collection device of claim 7 wherein distal end of syringe top acts as a stop to keep the needle carrier from exiting the proximal end of the syringe assembly when the carrier is pulled in the proximal direction.

9. The blood collection device of claim 6 wherein the seal assembly has a means for occluding blood flow when the collection tube is removed from the seal.

10. The blood collection device of claim 6 wherein the seal assembly is reversibly locked to the syringe assembly when blood is drawn.

11. A blood collection assembly for use with a collection tube, the blood collection assembly comprising:
    a syringe body having a cylindrical cavity with an inward taper on the distal end and an opening on the proximal end;
    a slidable needle assembly adapted for insertion into the proximal opening and stopped from exiting the distal end by the taper, the needle assembly having a double pointed needle secure within a needle carrier, wherein the distal end of the needle is used for a venipuncture and the proximal end for blood transfer to the collection tube;
    an insertable cylinder adapted for insertion into the cylindrical cavity of the syringe body and having a means for reversibly attaching to the proximal end opening of the syringe body;

a means for allowing blood to flow into the collection tube from the proximal end of the needle and for stopping blood flow when the collection tube is removed; and a means for securing both points of the needle within the combination of the syringe body and the slidable needle assembly, wherein a syringe top is irreversibly attached to the proximal end of the syringe body forming a stop to keep the needle carrier within the syringe body.

12. The blood collection device of claim 11 wherein the means for allowing and for stopping blood flow is an occluding seal comprising a flat seal and a with a compressible spring therebetween.

13. The blood collection device of claim 12 wherein reversible attachment means is a bayonet type mechanism.

14. The blood collection device of claim 12 wherein the occluding seal is secured within the insertable cylinder with retaining rings.

* * * * *